United States Patent [19]

Herold

[11] 4,392,589
[45] Jul. 12, 1983

[54] MULTIPLE-TUBE DISPENSER

[75] Inventor: Wolf-Dietrich Herold, Hechendorf, Fed. Rep. of Germany

[73] Assignee: ESPE Fabrik Pharmazeutischer Preparate GmbH, Seefeld, Fed. Rep. of Germany

[21] Appl. No.: 231,447

[22] Filed: Feb. 4, 1981

[30] Foreign Application Priority Data

Feb. 11, 1980 [DE] Fed. Rep. of Germany ....... 3005008

[51] Int. Cl.³ .............................................. B67D 5/42
[52] U.S. Cl. ....................................... 222/137; 222/39
[58] Field of Search ..................... 222/39, 41, 46, 129, 222/135, 137, 386, 390

[56] References Cited

U.S. PATENT DOCUMENTS

| 2,610,767 | 9/1952 | Gardner et al. ..................... 222/39 |
| 2,745,575 | 5/1956 | Spencer . |
| 2,826,339 | 3/1958 | Maillard . |
| 3,353,718 | 11/1967 | McLay . |
| 3,952,920 | 4/1976 | Bergman ............................ 222/137 |

FOREIGN PATENT DOCUMENTS

| 10913 | 9/1956 | Fed. Rep. of Germany . |
| 1411642 | 4/1961 | Fed. Rep. of Germany . |
| 6937543 | 9/1969 | Fed. Rep. of Germany . |
| 585633 | 3/1925 | France . |

Primary Examiner—Joseph J. Rolla
Assistant Examiner—Michael S. Huppert
Attorney, Agent, or Firm—Bacon & Thomas

[57] ABSTRACT

A multiple-tube dispenser contains components of a composition to be prepared by mixing the components at a fixed ratio. The tube cylinders are interconnected by a web and each have a discharge opening at their front end. Pistons provided in the tube cylinders are advanced in unison by plungers extending into the tube cylinders and interconnected by a common head portion. A threaded spindle extends through a bore provided in the head portion and engages a threaded bore provided in the web interconnecting the tube cylinders. The two bores are slotted in a direction perpendicular to the spindle axis so that the spindle may be inserted and removed at any position of the plungers relative to the tube cylinders. The web interconnecting the cylinders is made preferably of synthetic material and the bore in this web has an initially smooth inner surface in which the counter-thread is automatically tapped when the threaded spindle is inserted.

9 Claims, 6 Drawing Figures

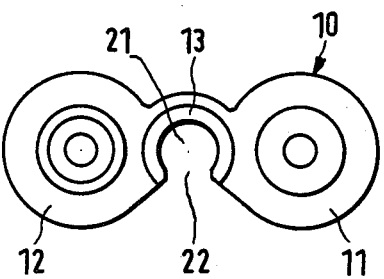
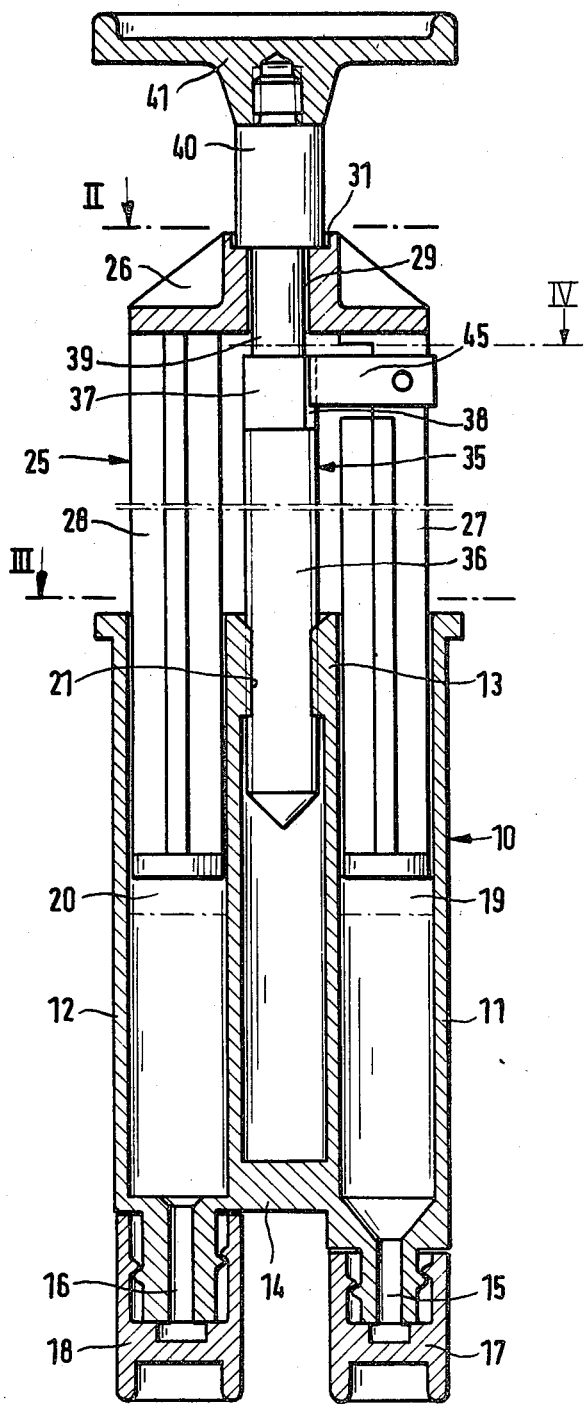

MULTIPLE-TUBE DISPENSER

BACKGROUND OF THE INVENTION

This invention relates to a multiple-tube dispenser. Devices of this type are used for simultaneously dispensing two or more components which react to form ready-to-use composition, such as dental cements or adhesive substances, which require the components to be discharged always at the same predetermined volume ratio.

U.S. Pat. No. 2,826,339 discloses a dispenser in which a body includes a plurality of nested cylindrical chambers all of which except the innermost are of annular cross-section. Pistons provided in the chambers are advanced by a commom plunger arrangement which is actuated by a threaded spindle engaging a closure member provided at the rear end of the innermost cylindrical chamber.

Due to the annular shape of the chambers, the pistons and the plunger arrangement, the known multiple-tube dispenser is very difficult to manufacture at reasonable tolerances, and the substantial friction of the annular pistons render the device hard to handle. An additional serious disadvantage resides in the face that, when the chambers have been emptied, a time-consuming procedure is required to remove the plunger arrangement with the threaded spindle by rotating the spindle all the way back in the reverse direction. Such a removal is necessary if it is required to reuse the threaded spindle, possibly also the plunger arrangement, whereas the tube body will regularly form a disposable one-way item.

Double-tube dispensers are known from German patent specification No. 1,411,642 and from German utility model specification No. 6,937,543, in which the plunger arrangement is moved into the tube body from the rear end thereof by a simple translatory movement. In this case, it would be possible to withdraw the plunger arrangement by a correspondingly simple straight movement if the plunger arrangement were to be re-used—which has not been considered. However, these known devices have no threaded spindle, so that it is required manually to apply a pressure on the plunger arrangement for dispensing the components. Depending on the viscosity of the components, this may again result in a difficult handling. Moreover, it is practically impossible with these devices to discharge exactly metered amounts of the components.

U.S. Pat. Nos. 2,745,575 and 3,353,718 disclose dispensing devices operating with a threaded spindle which may be released from its engagement with an internal thread by actuating a slider, whereupon the spindle may be removed from the tube. It is further known from French Pat. No. 585,633 to form the counter-thread for a threaded spindle by two portions of a tube cover, so that the spindle may be removed upon opening the cover and separating the two portions thereof. These three last-mentioned devices, however, are single-tube dispensers and therefore cannot be compared to multiple-tube devices in which the plunger arrangement required for simultaneously advancing all pistons necessarily complicates the overall structure.

It is an object of the invention to provide a multiple-tube dispenser which allows simple and quick assembly and disassembly of its various parts, so that some of them may readily be re-used. A further object of the invention is to provide a dispensing device which permits a simultaneous discharging of two or more components at a predetermined ratio in predetermined amounts. As a further object of the invention, a multiple-tupe dispenser is to be achieved which is inexpensive to manufacture and easy to handle.

SUMMARY OF THE INVENTION

A multiple-tube dispenser in accordance with the present invention comprises a body including two or more parallel tubes or cylinders interconnected by a web portion having a first bore. Each cylinder has at its front end a discharge opening, and a piston is slidably disposed in each cylinder. Each piston is adapted to be engaged by the front end of an associated plunger. The plungers are interconnected by a heat portion having a second bore. Simultaneous movement of all pistons relative to the cylinders is achieved by a threaded spindle which extends through the first bore and engages the second bore. Each bore has a slot which extends transversely to the axis of the spindle and permits the spindle to be inserted into, and removed from, the first and second bores along the said transverse direction. Thus, the spindle may be released by a simple lateral movement, whereupon the arrangement of plungers is free to be rearwardly withdrawn, no matter how far the plungers had been advanced in the cylinders. The structure according to the invention renders the assembly and disassembly of the spindle and plunger arrangement with the tube unit so simple that the producer of the components needs to provide only filled tube units, whereas the user requires just one single threaded spindle and one single plunger arrangement to be able to prepare the desired compositions at the required exact mixing ratio by simple manual operations.

Preferably, the first bore has initially a smooth inner surface, and the threaded spindle engages this bore in a self-tapping manner. This achieves the additional advantages that a comparatively inexpensive and simple molding tool is sufficient for making the tube unit and that threaded spindles of different pitches may be employed.

According to a further aspect of the invention, the second bore provided in the head portion has an enlarged portion at its end remote from the web portion, and the spindle has a flange engaging the enlarged portion, the diameter of the flange being larger than the width of the slot provided at the second bore. Furthermore, the web portion may be made of flexible material, and the width of the slot provided in the web portion may be smaller than the outer diameter of the spindle. By these measures, the threaded spindle is safely retained in the bores provided in the plunger arrangement and the tube unit.

The plunger arrangement preferably has a spring for snapping cooperation with a cam portion provided on the threaded spindle. This provides an audible, sensible and even visible indication of the individual spindle rotations, thereby ensuring an even more exact metering of the components discharged from the tubes.

In a further preferred embodiment, the spring and the cam portion are formed on the same side of the plunger arrangement on which the second bore in the head portion is provided, so as to prevent the spindle from being rotated in the wrong direction which would affect the proper metering in a subsequent discharging step. At the same time, the lateral removal of the spindle is further simplified.

BRIEF DESCRIPTION OF THE DRAWING

FIG. 1 is a longitudinal section through a double-tube dispenser.

FIG. 2 is an end view of the plunger arrangement taken in the direction of the arrow II in FIG. 1, with the threaded spindle removed.

FIG. 3 is an end view of the tube body taken in the direction of the arrow III in FIG. 1, with the plunger arrangement and the threaded spindle removed.

FIG. 5A shows the dispenser before the spindle is inserted and FIG. 5B shows the dispenser after it has been in operation and the spindle removed.

DETAILED DESCRIPTION OF PREFERRED EMBODIMENTS

Figure 4:
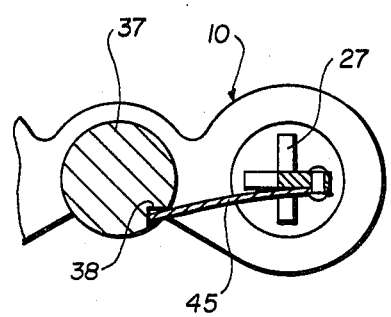
FIG. 4 is a section through the dispenser viewed in the direction of arrow IV in FIG. 1.
Figure 5A:
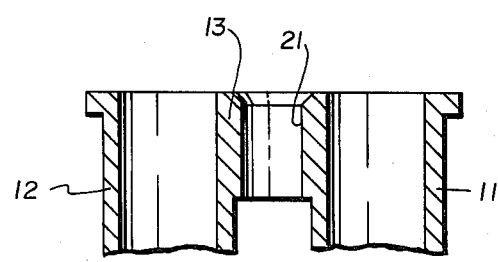
FIGS. 5A and 5B are sectional views of the rear portion of the tube with the plunger arrangement and threaded spindle removed.
Figure 5B:
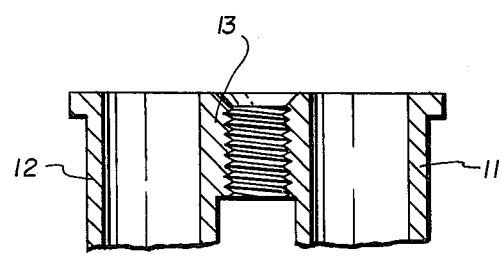

In the double-tube dispenser shown in the drawing, a tube body 10 includes two separate parallel cylinders 11 and 12 interconnected by two webs 13 and 14. The front ends of the cylinders 11 and 12 are provided with differently shaped discharge openings 15 and 16, respectively, which are closed by means of caps 17 and 18, respectively. Pistons 19 and 20 are movable within the cylinders 11 and 12, respectively.

One component of the composition to be prepared is filled in each chamber defined between the discharge opening and the piston of each cylinder. The tube body is filled by the manufacturer in such a manner that the pistons 19 and 20 are on equal levels.

As clearly shown in FIG. 3, the rear web 13 of the tube body has a bore 21 which opens laterally (towards the viewer in FIG. 1) through a slot 22. The width of the slot 22 is slightly smaller then the diameter of the bore 21. Initially, the interior wall of the bore 21 is smooth.

The dispenser furthermore includes a plunger arrangement 25 with two parallel plungers 27 and 28 interconnected by a common head 26. In the assembled condition of the dispenser, the plungers 27 and 28 extend into the cylinders 11 and 12, respectively, and their front ends engage the rear faces of the pistons 19 and 20, respectively.

As clearly shown in FIG. 2, the head 26 has a bore 29 which opens laterally (towards the viewer in FIG. 1) through a slot 30. The width of the slot 30 is equal to the diameter of the bore 29. An enlarged portion 31 is provided at the rear end (at the upper end in FIG. 1) of the bore 29.

The pistons 27, 28 are advanced within the cylinders 11, 12 by a threaded spindle 35 which includes the following sections, starting from the front end (the lower end in FIG. 1):

a threaded section 36 for engaging the bore 21 provided in the web 13 of the tube body 10;

a detent section 37 having an axially extending groove 38 (or alternatively an axially extending projection, not shown);

a cylindrical section 39 for engaging the bore 29 in the head 26;

a flange 40 for engaging the enlarged portion 31; and an elongate handle 41.

The web 13 is resilient, and the thread of the spindle 35 as well as the bore 21 provided in the web 13 are of such materials and dimensions that the threaded spindle, when rotated, taps its own counter-thread into the wall of the bore 21.

A leaf spring 45 is mounted on the plunger 27, and a short portion at the free end of the spring is bent in a direction pointing away from the viewer in FIG. 1. This bent portion cooperates with the axial groove 38 (or the projection, if a projection is provided instead of the groove) in such a manner that an audible and sensible detent action is achieved each rotation of the threaded spindle 35. In addition, the axial groove 38 (or the projection) can serve as a visible indication of the spindle position. These measures provide a very accurate metering of the plunger advance, thus of the amounts of components discharged.

The diameter of the cylindrical section 39 of the threaded spindle 35 is somewhat smaller than the diameter of the bore 29 in the head 26 and than the width of the slot 30. The diameter of the flange 40 is somewhat smaller than the diameter of the enlarged portion 31, but greater than the width of the slot 30. As a result, the threaded spindle rotates with ease in the head and it may be easily removed through the lateral slot 30 once the flange 40 has been withdrawn out of the rear end of the head. In order to lift the flange 40 out of the enlarged portion 31, the threaded spindle must be screwed back against the advancing direction of the plungers by a partial rotation. By this reverse rotation, the leaf spring 45, which is mounted on that side of the plunger arrangement 25 on which the slot 30 is disposed in the head 26 and which is shaped such that it locks the threaded spindle 35 against being completely unscrewed from the tube body, is biassed by the axial groove 38 (or the projection) in the locking direction. During the mentioned partial rotation in the reverse direction, the spring 45 will lift the threaded spindle 35 in the lateral direction through the slot 30 out of the head 26.

The web 13 in the tube body 10 is resilient so that the threaded section 36 of the spindle 35 may be laterally removed through the slot 22 provided in the web 13 by overcoming the resilient bias of the web.

In use, the filled tube body is supplied by the producer, and the only thing the user has to do is to move the plunger arrangement 25 with the threaded spindle 35 inserted into the tube body from the rear side thereof. By rotating the threaded spindle, e.g. in the clockwise direction, a counter-thread is automatically tapped into the web 13 of the tube body. Alternatively, particularly when the device is automatically assembled, the threaded spindle 35 may be inserted as the last item in the transverse direction through the slots 22 and 30.

For dispensing the content of the tube body, the two caps 17 and 18 are removed, and the threaded spindle 35 is rotated by one or more turns by means of the handle 41 so that the components are discharged from the two discharge openings 15 and 16 in the predetermined mixing ratio. By an according selection of the cylinder cross-sections, this ratio may be determined for the purpose for which the device is to be used.

When the tube body is empty, the threaded spindle may be removed laterally of its axis through the slots 22 and 30 with one grasp, as decribed above, whereupon the plunger arrangement 25 may be withdrawn rearwardly in the axial direction. The plunger arrangement and the threaded spindle may then be inserted into the next filled tube body, while the empty tube body is disposed of. In view of this re-using facility, the plunger arrangement and the threaded spindle are made of a durable material, preferably metal.

In an alternative embodiment, the plunger arrangement 25 is made of synthetic material. In this case, it is advantageous to produce the leaf spring 45 of the same material as an integral portion of the plunger 27. Also in this case, the slot 30 in the head 26 (FIG. 2) may be somewhat narrower than the diameter of the smooth cylindrical section 39 of the spindle 35, similar to the slot 22 in the web 13 of the tube body 10 as shown in FIG. 3, so that the threaded spindle may be inserted into the bore of the head by a snap-action in elastically widening the slot 30. This provides an additional means for maintaining the spindle in the plunger arrangement.

In case also the threaded spindle 35 is made of synthetic material, the handle 41 is made integral with the spindle, in contrast to what is shown in FIG. 1. In view of the greater tolerances occurring when the threaded spindle is molded from synthetic resin, the diameters of the spindle and the bore 21 in the web 13 of the tube body 10 are selected so as to ensure a self-tapping engagement of the threaded spindle in this bore even in case of a fine-pitch thread. Notwithstanding such dimensions, the spindle will be rotatable with sufficient ease because excessive pressures are avoided by the slot 22 and the resiliency of the tube body material.

In case all parts of the multiple-tube dispenser are made of synthetic material, as described for this embodiment, the entire dispenser may be used as a one-way disposable device. In this case, the above-described structure has the advantage of being easily manufactured. Particularly in automatic production, the lateral inserting of the spindle is more easily performed than a screwing step, in which it would be particularly problematic to recognize the position in which the plungers 27, 28 abut the pistons 19, 20 and the screwing motion must be terminated.

I claim:

1. A multiple-tube dispenser comprising
   (a) a body including at least two parallel cylinders, each having a discharge opening at a front end thereof, a piston slidably disposed in each cylinder, and a web portion of flexible material interconnecting said cylinders and having a first bore;
   (b) pressing means including a head portion with a second bore, and a number of plungers equal to the number of said cylinders, said plungers being interconnected by said head portion, and each having a front end for engaging an associated one of said pistons; and
   (c) a threaded spindle extending through said second bore and engaging said first bore for causing simultaneous movement of said pistons relative to said cylinders;
   (d) said first and second bores having first and second slots, respectively, extending in a direction transverse to the axis of said spindle for permitting said spindle to be inserted into, and removed from, said first and second bores along said transverse direction, the width of said first slot being smaller than the outer diameter of said spindle.

2. The dispenser of claim 1, wherein said first bore has an initially smooth inner surface, said threaded spindle engaging said first bore in a self-tapping manner.

3. The dispenser of claim 1, wherein said second bore has an enlarged portion at its end remote from said web portion and said spindle has a flange engaging said enlarged portion, the diameter of said flange being larger than the width of said second slot.

4. The dispenser of claim 1, wherein said pressing means has a spring for snapping cooperation with a cam portion provided on said spindle.

5. The dispenser of claim 4, wherein said spring and said cam portion are formed so as to prevent substantial rotation of said spindle in a direction in which said plungers are moved out of said cylinders.

6. The dispenser of claim 5, wherein said spring is disposed on the same side of said pressing means on which said second slot is provided in said head portion.

7. The dispenser of claim 1, wherein said pressing means is made of flexible material and the width of said second slot is smaller than the outer diameter of said spindle.

8. A multiple tube dispenser comprising
   (a) a body including at least two parallel cylinders each having a discharge opening at a front end thereof, a piston slidably disposed in each cylinder, and a web portion interconnecting said cylinders and having a first bore;
   (b) pressing means including a head portion with a second bore, and a number of plungers equal to the number of said cylinders, said plungers being interconnected by said head portion, and each having a front end for engaging an associated one of said pistons; and
   (c) a threaded spindle existing through said second bore and engaging said first bore for causing simultaneous movement of said pistons relative to said cylinders;
   (d) said first and second bores having first and second slots, respectively, extending in a direction transverse to the axis of said spindle, for permitting said spindle to be inserted into, and removed from, said first and second bores along said transverse direction;
   (e) said second bore having an enlarged portion at its end remote from said web portion and said spindle having a flange engaging said enlarged portion, the diameter of said flange being larger than the width of said second slot.

9. A multiple-tube dispenser comprising
   (a) a body including at least two parallel cylinders, each having a discharge opening at a front end thereof, a piston slidably disposed in each cylinder, and a web portion interconnecting said cylinders and having a first bore;
   (b) pressing means made of flexible material and including a head portion with a second bore, and a number of plungers equal to the number of said cylinders, said plungers being interconnected by said head portion, and each having a front end for engaging an associated one of said pistons; and
   (c) a threaded spindle extending through said second bore and engaging said first bore for causing simultaneous movement of said pistons relative to said cylinders;
   (d) said first and second bores having first and second slots, respectively, extending in a direction transverse to the axis of said spindle for permitting said spindle to be inserted into, and removed from, said first and second bores along said transverse direction, the width of said second slot being smaller than the outer diameter of said spindle.

* * * * *